United States Patent
Dennerlein

(10) Patent No.: US 8,824,765 B2
(45) Date of Patent: Sep. 2, 2014

(54) METHOD FOR ACQUIRING A 3D IMAGE DATASET ASSOCIATED WITH AN IMAGE OBJECT FOR REDUCING BEAM ARTIFACTS

(75) Inventor: Frank Dennerlein, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 73 days.

(21) Appl. No.: 13/478,342

(22) Filed: May 23, 2012

(65) Prior Publication Data

US 2012/0301008 A1 Nov. 29, 2012

(30) Foreign Application Priority Data

May 26, 2011 (DE) .......................... 10 2011 076 547

(51) Int. Cl.
| | |
|---|---|
| *G06K 9/00* | (2006.01) |
| *G06T 11/00* | (2006.01) |
| *A61B 6/00* | (2006.01) |
| *A61B 6/03* | (2006.01) |
| *A61B 6/02* | (2006.01) |

(52) U.S. Cl.
CPC ......... *G06T 11/006* (2013.01); *G06T 2211/432* (2013.01); *A61B 6/5205* (2013.01); *G06T 2211/421* (2013.01); *A61B 6/032* (2013.01); *A61B 6/5258* (2013.01); *G06T 2211/416* (2013.01); *A61B 6/027* (2013.01)
USPC ........................................................ 382/131

(58) Field of Classification Search
None
See application file for complete search history.

(56) References Cited

U.S. PATENT DOCUMENTS

| | | | |
|---|---|---|---|
| 2006/0067457 A1* | 3/2006 | Zamyatin et al. .................. 378/4 |
| 2006/0115040 A1 | 6/2006 | Chen | |
| 2009/0110139 A1* | 4/2009 | Noshi et al. ........................ 378/4 |
| 2010/0158194 A1 | 6/2010 | Pack | |
| 2010/0232565 A1* | 9/2010 | Ye et al. ............................. 378/5 |
| 2010/0283779 A1* | 11/2010 | Chiang et al. ................. 345/419 |
| 2011/0085637 A1* | 4/2011 | Boese et al. ....................... 378/4 |
| 2011/0091085 A1 | 4/2011 | Dennerlein | |
| 2012/0301008 A1* | 11/2012 | Dennerlein ................... 382/132 |
| 2013/0028498 A1* | 1/2013 | Dennerlein et al. .......... 382/132 |
| 2013/0077847 A1* | 3/2013 | Hansis et al. ................. 382/131 |

FOREIGN PATENT DOCUMENTS

WO  WO 2011/148277  * 12/2011

OTHER PUBLICATIONS

Michel Defrise et al., "Truncated Hilbert transform and image reconstruction from limited tomographic data" Inverse Problems vol. 22 No. 3 2006 Inverse Problems 22 1037 doi:1088/0266-5611/22/3/019, Available online: http://iopscience.iop.org/0266-5611/22/3/019.*

You Jiangsheng, and Gengsheng L. Zeng. "Hilbert transform based FBP algorithm for fan-beam CT full and partial scans." Medical Imaging, IEEE Transactions on 26.2 (2007): 190-1.*

(Continued)

*Primary Examiner* — Tahmina Ansari

(57) ABSTRACT

A method for acquiring a 3D image dataset is proposed. A 3D X-ray image dataset of an image object is acquired during scanning of a partial circle by X-ray radiation source and X-ray radiation detector. A first and a second 3D image datasets are calculated from the acquired image dataset. Redundancies are eliminated by averaging the first and second 3D image datasets. A filtering that is antisymmetric in respect of a center of symmetry is performed in respect of the 2D image datasets in calculating the second 3D image dataset. Said filtering has a row-by-row Hilbert transform. Suitable weights can be specified based on an axis defined in space.

2 Claims, 2 Drawing Sheets

(56) References Cited

OTHER PUBLICATIONS

Ikuko Arai, Hiroyuki Kudo, Frédéric Noo, Michel Defrise and Jed D. Pack; A New Class of Super-Short-Scan Algorithms for Fan-Beam Reconstruction Arai et al.; 2005 IEEE Nuclear Science Symposium Conference Record, Seiten 2296-2300; Puerto Rico; Magazine; 2005.

Brian E. Nett et al. Arc based cone-beam reconstruction algorithm using an equal weighting scheme Journal of X-Ray Science and Technology 15 (2007) pp. 19-48 IOS Press; Magazine; 2007.

M. Defrise and R. Clack A Cone-Beam Reconstruction Algorithm Using Shift-Variant Filtering and Cone-Beam Backprojection 186 IEEE Transactions on Medical Imaging, vol. 13 No. 1, Mar. 1994; Others; 1994.

Lei Zhu et al. A short-scan reconstruction for cone-beam CT using shift-invariant FBP and equal weighting Med. Phys. 34 (11), Nov. 2007 Assoc. Phys. Med.; Magazine; 2007.

* cited by examiner

METHOD FOR ACQUIRING A 3D IMAGE DATASET ASSOCIATED WITH AN IMAGE OBJECT FOR REDUCING BEAM ARTIFACTS

CROSS REFERENCE TO RELATED APPLICATIONS

This application claims priority of German application No. 10 2011 076 547.6 filed May 26, 2011, which is incorporated by reference herein in its entirety.

FIELD OF INVENTION

The invention relates to a method for acquiring a 3D (X-ray) image dataset associated with an image object. A 3D image dataset is a dataset in which volume elements (voxels) in the region of the image object are assigned grayscale values which are a metric for the attenuation of X-ray radiation by the image object in the region of the volume element.

BACKGROUND OF INVENTION

Such a 3D image dataset is obtained when a plurality of 2D image datasets are recorded. For this purpose a unit consisting of X-ray radiation source and X-ray radiation detector must be moved in unison successively into a plurality of rotational positions about an axis of rotation, and a 2D image dataset is acquired at each rotational position.

Calculating the 3D image dataset is very simple if the rotational positions encompass the entire range of 360° in equal increments. Frequently, however, there is merely what is termed a short-scan or partial circle scanning trajectory, with scanning taking place over a range of 200° for example. Then the data are redundant, but not to the same extent. For example, image data acquired at the angle of 10° correspond to data at an interval around 190°. With mutually corresponding image data the positions of X-ray radiation source and a respective detector element are simply interchanged, yet the X-ray beams pass through the image object simply in the reverse direction, but on the same paths. It is self-evident that these redundancies in the calculation of a 3D image dataset associated with the image object need to be eliminated.

The technique according to Feldkamp known as filtered backprojection exists for such partial circle scanning trajectories, wherein the redundancy is removed by means of a weighting of the detector content, said weighting being referred to as the Parker weights. Although computationally efficient, this approach only contains approximations. So-called cone beam artifacts are visible in the thus resulting 3D image dataset.

It is known from the publication by Zhu et al., "A short-scan reconstruction for cone-beam CT using shift-invariant FBP and equal weighting", Med. Phys. 34 (11), November 2007, pages 4422 to 4438, to eliminate the redundancies as follows: A filtered backprojection is performed in respect of the 2D image dataset in order to acquire a first 3D image dataset in which mutually corresponding data from the 2D image datasets are possibly incorporated twice (i.e. once redundantly). Said redundancy is now compensated for as follows: An additional calculation is performed in order to acquire a second 3D image dataset on the basis of the 2D image datasets, in which calculation the data included twice in the first 2D image dataset are not incorporated at all. The two 3D image datasets are then averaged, such that all the data are included once in the resulting 3D image dataset.

In this way a method according to the preamble of the independent claim is obtained.

A disadvantage of the method of Zhu et al. is that the problem referred to as axial truncation is only dealt with approximately. Compared to the Feldkamp approach, image errors are produced at the top and bottom end of the field of view. Furthermore it does not permit the volume to be calculated only in sections of axial layers.

The article by Arai et al., "A New Class of Super-Short-Scan Algorithms for Fan-Beam Reconstruction", IEEE Medical Imaging Conference Record, Wyndham El Conquistador, Puerto Rico, pages 2296 to 2300 (2005), describes an image reconstruction algorithm in which a Hilbert transform is followed by a derivation.

SUMMARY OF INVENTION

It is the object of the present invention to disclose a method for acquiring a 3D image dataset associated with an image object, which method moreover, like the method of Zhu et al., likewise significantly reduces the cone beam artifacts compared to the partial circle Feldkamp approach, though it does so without the cited disadvantages persisting.

The object is achieved by a method having the features recited in the claims.

Accordingly the basic idea of Zhu et al., namely to calculate two 2D image datasets and then to average these, is taken up. In the present approach, step b2), i.e. performing a calculation in order to acquire the second 3D image dataset, is performed in such a way that the 2D image datasets are subjected to a filter that is antisymmetric in respect of a center of symmetry in terms of a convolution. A backprojection is then applied. The antisymmetry corresponds to a point symmetry.

In contrast to the approach according to Zhu et al., the filtering (convolution) therefore does not take place in the 3D image dataset at the time of its calculation, but already prior thereto in the 2D image datasets. The truncation problem can be avoided in this way. For example, the filter can be defined row by row (or, conversely, column by column), in which case there exists by nature no truncation problem.

In the method according to the invention, a derivative is preferably calculated in step b2) after the backprojection (and moreover in accordance with the finite differences method). In this way the advantages of the method of Zhu et al. can be used simultaneously with those of the method of Arai et al. However, the derivation is referred to the 3D image dataset, whereas the filtering relates to the 2D image dataset.

The filtering is performed in particular with the aid of a Hilbert transform, preferably a row-by-row Hilbert transform. The Hilbert transform is antisymmetric per se and on account of the simple calculation is therefore particularly suitable as a filter to be employed in the present situation.

Because the Hilbert transform itself is antisymmetric, symmetric weightings are preferably used in respect of the center of symmetry. The weightings enable provision to be made for a precise implementation of the backprojection.

The inventor of the present invention has recognized in particular that it is possible to define an axis in three-dimensional space, which axis twice intersects an angular range (the partial circle) in which all the rotational positions lie and over which a 2D image dataset has been acquired. The weightings in the case of the Hilbert transform can then relate pixel by pixel to the angle at which the measurement beam stands in relation to said axis, i.e. the beam in relation to a detector element of the detector, the detector element corresponding to the respective pixel. Such weightings are particularly useful on account of geometric considerations. If the weightings relate to the respective angle, the redundancies resulting from mutually corresponding pixels from different projections cancel one another out exactly, i.e. said redundancies are not incorporated at all in the second image dataset.

BRIEF DESCRIPTION OF THE DRAWINGS

A preferred embodiment variant of the invention is described in more detail below with reference to the drawing, in which.

DETAILED DESCRIPTION OF INVENTION

Figure 2:
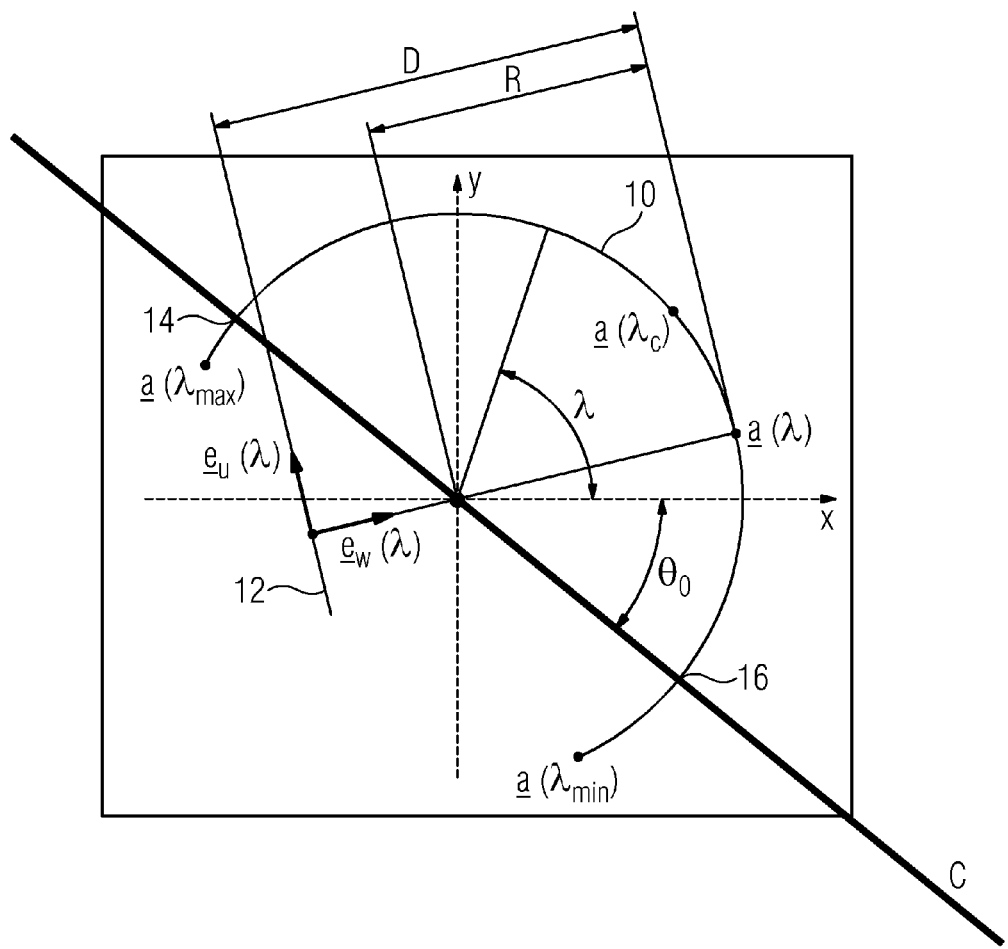
FIG. 2 is a diagram intended to illustrate the variables being incorporated in formulae used in the present solution.

An X-ray radiation source and an X-ray radiation detector are co-rotated about a center of rotation which in FIG. 2 is the origin of a coordinate system. FIG. 2 shows the trajectory 10 along which the X-ray radiation source travels as $a(\lambda)$, the position of the X-ray radiation detector 12 being shown simultaneously at a specific $a(\lambda)$. The X-ray radiation detector 12 is spaced apart from the X-ray radiation source by the distance D, and the X-ray radiation source rotates at the radius R around the origin. The coordinates of the detector are u and v, and each position of the X-ray radiation detector is assigned direction vectors $e_u(\lambda)$ and $e_u(\lambda)$ in the plane of the detector, and is yielded as a normal vector.

Figure 1:
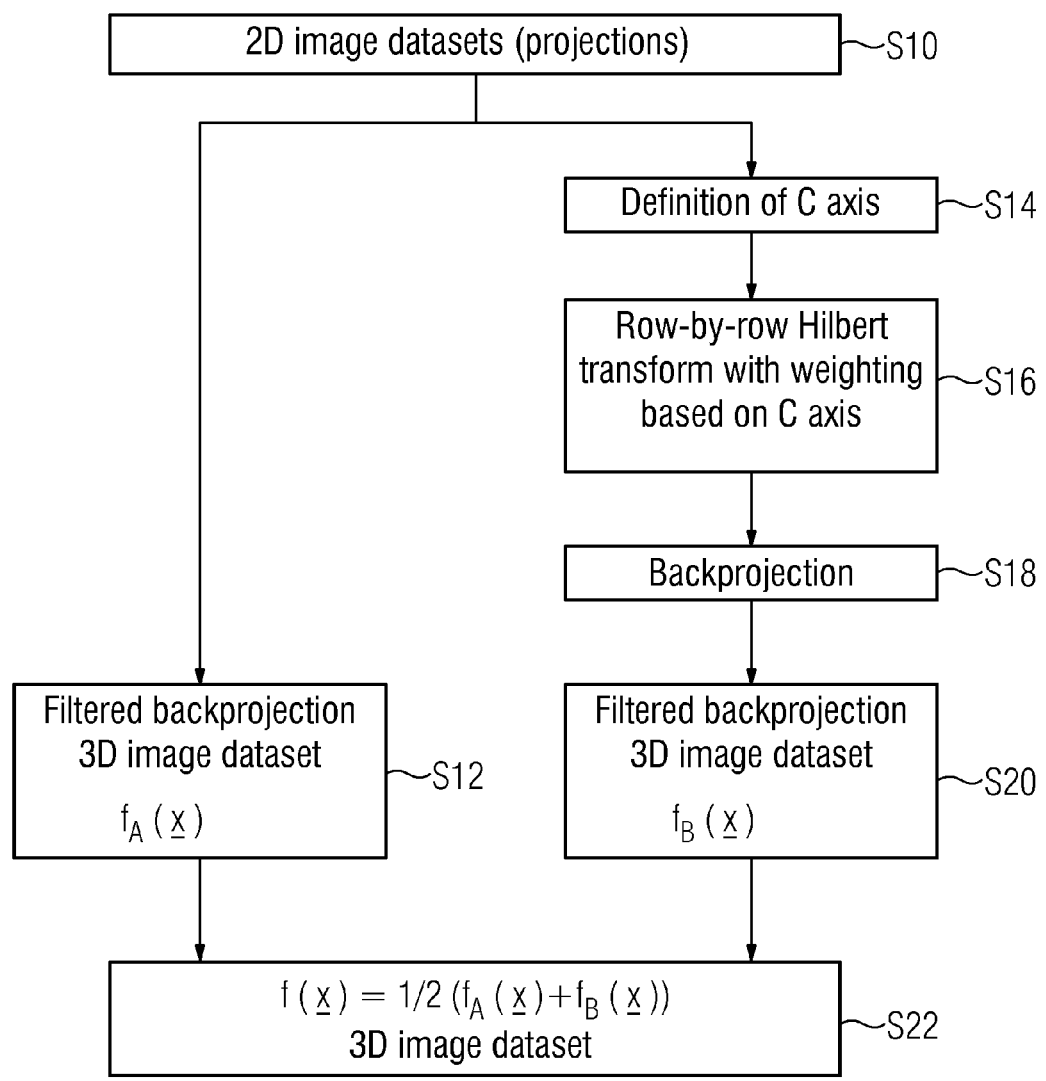
FIG. 1 is a flowchart intended to explain an embodiment variant of the method according to the invention.

X-ray images (2D image datasets) are acquired at a plurality of positions on the trajectory 10, with the grayscale values or detector values $g(\lambda,u,v)$. The 2D image datasets, which are also referred to as projections, are acquired in step S10 according to FIG. 1.

The method now divides into two different branches in which calculations are performed. The calculations in the two branches can take place in parallel with one another.

A filtered backprojection is calculated in step S12. In this case (cosine-)weighted grayscale values $g_w(\lambda,u,v)$ are used according to the formula:

$$g_w(\lambda, u, v) = \frac{D}{\sqrt{D^2 + u^2 + v^2}} g(\lambda, u, v),$$

and in conjunction with a kernel $h_r$ of a ramp filter a 3D image dataset is produced as an assignment of grayscale values to volume elements with the coordinate x according to the formula:

$$f_A(\underline{x}) = \int_{\lambda_1}^{\lambda_2} d\lambda \frac{RD}{[R - \underline{x} \cdot \underline{e}_w(\lambda)]^2} \int_{-\infty}^{\infty} du h_r(u^* - u) g_w(\lambda, u, v^*).$$

This first 3D image dataset contains redundancies, i.e. data values which are also recorded in other projections, which correspond to one another and for these projections are incorporated once in each case in the calculation, i.e. twice in total.

The aim is to compensate for these redundancies by computing a second 3D image dataset $f_B(\underline{x})$ in which the redundancies cancel one another out.

For this purpose an axis C is initially defined. In order to define the axis it is simply necessary for it to intersect the trajectory 10 twice, namely at the point 14 and at the point 16. The exact position of the axis C is not significant. The axis C is defined by means of an angle $\theta_0$ that it assumes relative to the x-axis of the coordinate system. The axis C is defined in step S14.

The variables $g_w(\lambda,u,v)$ are subjected to a Hilbert transform with a weighting of $|\sin(\lambda-\text{atan}(u/D)-\theta_0)|$, and if $h_h$ is the filter kernel, we calculate a provisional function $t(\underline{x})$ according to:

$$t(\underline{x}) = \frac{1}{2\pi} \int_{\lambda_1}^{\lambda_2} d\lambda \frac{R}{[R - \underline{x} \cdot \underline{e}_w(\lambda)]} \int_{-\infty}^{\infty} du h_h(u^* - u) \frac{g_w(\lambda, u, v^*)}{|\sin(\lambda - a\tan(u/D) - \theta_0)|}.$$

With the back integral, which runs from $-\infty$ to $+\infty$, the formula (3) corresponds to a row-by-row Hilbert transform with a weighting based on the axis C, i.e. it contains the sub-step S16. In the front integral it includes backprojection in sub-step S18. In the case of a numeric integration for calculating the integral for $t(\underline{x})$, signal strengths in the denominator can be replaced by a minimum value.

The row-by-row Hilbert transform is free of an axial truncation problem and therefore advantageous. It is antisymmetric (point symmetry through 4=0). Redundancies in the data values cancel one another out exactly on account of their antisymmetry. Because the Hilbert transform is already antisymmetric, the weights by which the $g_w(\lambda,u,v^*)$ are multiplied are chosen as symmetric. What is involved is a sine in which the coordinate u is incorporated, the angle $\lambda$ is incorporated, and wherein the thus resulting angle $\lambda-\alpha\tan(u/D)$ is then also shifted through $\theta_0$. It has been demonstrated that precisely these weights result in an optimal reconstruction, in other words that the 3D image dataset $f_B(x)$ resulting overall corresponds best to the actual circumstances of the image object. In order to acquire the 3D image dataset $f_B(x)$, a derivative is additionally calculated in step S20, and specifically in accordance with the finite differences method, i.e. the following formula is used:

$$f_B(\underline{x}) = \frac{t(\underline{x} + \varepsilon(\cos\theta_0, 0)) - t(\underline{x} - \varepsilon(\cos\theta_0, \sin\theta_0, 0))}{2\varepsilon}$$

Now that a first 3D image dataset $f_A(\underline{x})$ has been acquired in which redundancies are also redundantly included, i.e. have not been eliminated with the aid of Parker weights, and since a second 3D image dataset $f_B(\underline{x})$ has been acquired in which the redundant data values cancel one another out exactly, the average value of said two 3D image datasets $f_A(\underline{x})$ and $f_B(\underline{x})$ can be calculated in step S22 as $f(\underline{x})=1/2(f_A(\underline{x})+f_B(\underline{x}))$.

The thus acquired 3D image dataset has no further traces of the redundancies, no cone beam artifacts, and furthermore no axial truncation problems are in evidence either.

The invention claimed is:
1. A method for acquiring a 3D image dataset of an image object, comprising:
acquiring a plurality of 2D image datasets of the image object at a plurality of rotational positions respectively on a trajectory by an X-ray unit, the X-ray unit comprising an X-ray radiation source and an X-ray radiation detector that can be moved in unison into the plurality of rotational positions along the trajectory about an origin of a coordinate system;
acquiring a first 3D image dataset by a filtered backprojection of the 2D image datasets, wherein data value redun- dancies of the 2D image datasets are mutually incorporated in the first 3D image dataset;

acquiring a second 3D image dataset by filtering the 2D image datasets that is antisymmetric in respect of a center of symmetry and by a subsequent backprojection of the filtered 2D image datasets, wherein the data value redundancies of the 2D image datasets are not incorporated in the acquired second 3D image dataset; and calculating an averaged 3D image dataset by averaging the acquired first and second 3D image datasets, wherein the data value redundancies are eliminated in the averaged 3D image, wherein the second 3D image dataset is acquired by:
defining an axis in a three-dimensional space by an angle relative to an x-axis of the coordinate system, wherein the axis intersects twice with the trajectory, filtering the 2D image datasets by Hilbert transform with symmetric weightings based on the axis, wherein the symmetric weightings relate to the angle at which the axis stands at one of the plurality of rotational positions relative to the X-ray radiation detector, and subsequently backprojecting the filtered 2D image datasets.

2. The method as claimed in claim 1, wherein a derivative is calculated after the subsequent backprojection of the filtered 2D image datasets for acquiring the second 3D image dataset.

* * * * *